United States Patent

Mooberry et al.

Patent Number: 5,959,120
Date of Patent: Sep. 28, 1999

[54] ACETATE ESTER COMPOUNDS

[75] Inventors: Jared B. Mooberry, Rochester; Thomas E. Gompf, Penfield; Brian H. Johnston, Rochester, all of N.Y.

[73] Assignee: Eastman Kodak Company, Rochester, N.Y.

[21] Appl. No.: 08/873,651

[22] Filed: Jun. 12, 1997

[51] Int. Cl.$^6$ .................... C07D 249/18; C07D 403/04; C07D 403/06; C07C 323/23
[52] U.S. Cl. .................... 548/253; 548/254; 548/255; 548/261; 548/262.4; 548/264.2; 548/264.8; 548/267.6; 548/338.5; 548/375.1; 548/376.1; 560/16; 560/34; 560/43
[58] Field of Search ................... 548/255, 253, 548/257, 262.4, 264.8, 267.2, 267.6, 338.5, 375.1, 376.1; 560/16, 34, 43

[56] References Cited

U.S. PATENT DOCUMENTS

| | | | |
|---|---|---|---|
| 4,076,533 | 2/1978 | Ota et al. ........................... | 96/56.5 |
| 4,095,984 | 6/1978 | Sueyoshi et al. ................... | 96/100 |
| 4,105,656 | 8/1978 | Nakamara et al. .................. | 260/239.9 |
| 4,241,168 | 12/1980 | Arai et al. .......................... | 430/503 |
| 4,262,087 | 4/1981 | Quaglia ............................... | 430/503 |
| 5,521,318 | 5/1996 | Yamakawa et al. ................. | 548/261 |

FOREIGN PATENT DOCUMENTS

| | | |
|---|---|---|
| 0 087 388 | 8/1983 | European Pat. Off. . |
| 7-281373 | 10/1995 | Japan . |
| 1603233 | 11/1981 | United Kingdom . |

*Primary Examiner*—Johann Richter
*Assistant Examiner*—Jane C. Oswecki
*Attorney, Agent, or Firm*—Arthur E. Kluegel

[57] ABSTRACT

The present invention provides an acetate ester compound of formula (III),

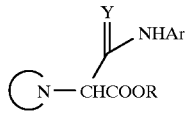

(III)

a process for synthesizing compound (III), and a process for using that compound to prepare a pyrazolone compound, where the substituent definitions are as defined in the Summary of the Invention.

8 Claims, No Drawings

ACETATE ESTER COMPOUNDS

FIELD OF THE INVENTION

This invention relates to 2-azolyl-2-arylcarbamoyl or 2-azolyl-2-arylthiocarbamoyl acetate esters, a process for making such compounds, and a process for forming pyrazolone compounds from such esters.

BACKGROUND OF THE INVENTION

There has been a continuing need for couplers that release development inhibitors (so-called Development Inhibitor Releasing or "DIR" couplers). In particular, such couplers that form magenta dye upon release of the inhibitor are desirable for use in magenta dye imaging layers of silver halide photographic elements. Especially useful would be magenta dye-forming pyrazolone couplers capable or releasing azole development inhibitor groups. A number of patents have disclosed such compounds. A problem with such compounds is that their synthesis on a commercial scale has proven exceedingly difficult. Proposed synthesis routes have provided poor yields, employed carcinogenic raw materials, or have otherwise been unsuccessful.

The processes of the art suggest first forming the pyrazolone moiety and then appending the N-heterocycle. U.S. Pat. No. 4,095,984 describes a certain benzotriazole inhibitor group appended to any coupler moiety. Synthesis Example 4 at column 23 describes a method of preparing the coupler employing hexamethylphosphotriamide. This material is a carcinogen and its use is therefore undesirable. It is further described that the temperature is high (110° C.), the reaction is slow (8 hrs.), and the yield is about 30%, all of which are unsatisfactory for commercial purposes. The same type of synthesis is shown in U.S. Pat. No. 4,076,533.

U.S. Pat. No. 4,241,168 shows a synthesis not involving the formation of an azolyl acetate ester in which the yield is low (about 30%). U.S. Pat. No. 4,105,656 shows a synthesis not involving the formation of an azolyl acetate ester in which the yield is about 15%. GB Patent 1,603,223 describes some of the difficulties in manufacturing such pyrazolone couplers. Generally, these methods involve attaching the desired azole group to the coupler moiety as a last step. U.S. Pat. No. 4,262,087 and EP 0 087 388 use a conventional chloroacetoacetate route rather than using an azolylacetate.

U.S. Pat. No. 5,521,318 discloses a process for making yellow rather than magenta couplers utilizing a chloro ketone rather than a chloro ester and using an isocyanate rather than an isothiocyanate as preferred in this invention.

A problem to be solved is to provide a process for making 2-azolyl-2-arylcarbamoyl acetate esters and 2-azolyl-2-arylthiocarbamoyl acetate esters and a process for using such compounds which processes are simple, safe, and provide good yields.

SUMMARY OF THE INVENTION

The present invention provides a process for synthesizing an acetate ester having formula (III)

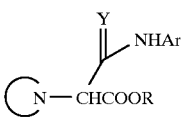
(III)

comprising reacting a compound of the formula (I)

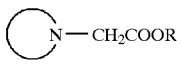
(I)

with a compound of the formula (II)

$$ArN=C=Y \quad (II)$$

in the presence of a base,
wherein:
R is an alkyl or aryl group;
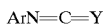 represents the nonmetallic atoms necessary to complete an azole ring;
Ar represents an aromatic carbocyclic or an aromatic heterocyclic group;
and Y represents an atom of oxygen or sulfur.

The invention also provides the intermediate (III) and a process for using compound (III) to prepare pyrazolone compound (IV).

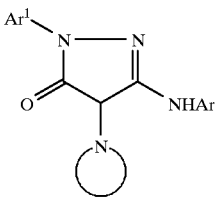
(IV)

wherein $Ar^1$ represents an aromatic carbocyclic or an aromatic heterocyclic group.

The invention provides intermediate (III), a process for making intermediate (III), and a process for using such compounds to prepare compounds of formula (IV) which processes are simple, safe, and provide good yields.

DETAILED DESCRIPTION OF THE INVENTION

As described in the Summary of the Invention, the invention provides an intermediate compound (III), a method of synthesizing compound (III), and a method of using compound (III) to synthesize compound (IV).

The R group of the invention is an alkyl or aryl group, typically an alkyl group such as one having up to 6 carbon atoms, for example methyl or ethyl. Since this group does not remain in the final product, there is not much point in using an unnecessarily complex or high molecular weight substituent.

Ar represents an aromatic carbocyclic or an aromatic heterocyclic group. Particularly for photographic applications, it is desirable for the Ar group to contain one or more substituents as provided hereafter. In particular, p-nitrophenyl or a phenyl group containing a hydrophobic alkyl chain are desirable.

The balance of the nitrogen heterocyclic ring, represented by ◯ may represent any atoms necessary to complete an azole ring. The ring may contain more than one nitrogen atom and may contain other non carbon atoms. Examples include imidazoles, pyrazoles, triazoles, oxazoles, and tetrazoles. Particularly desirable are benzotriazoles. The ring may also include a fused ring, comprising for example a benzotriazole.

The group "Y" can be an atom of oxygen or sulfur, thus forming either a carbamoyl or thiocarbamoyl group. Sulfur is preferred when the compound (III) is subsequently used to prepare compound (IV) as shown. When the thiocarbamoyl is used, the subsequent reaction with arylhydrazine proceeds under very mild conditions.

The group $Ar^1$ may be a carbocyclic or heterocyclic aromatic group. Preferably, such group is substituted with one or more groups selected from halogen, nitro, alkyl, acyloxy, carboxy, sulfonyl, sulfamoyl, sulfonamido, carbamoyl, or carbonamido groups. Desirably, $Ar^1$ is a phenyl group such as one substituted with a nitro or halogen group. Particularly desirable is a 2,4,6-trichlorophenyl group.

The base used to form compound III may be any of those commonly used in synthesis chemistry such as amine compounds and the hydroxides, carbonates and alkoxides of the alkali metals or ammonium. A particularly useful base is an amine salt of an alkali metal, such as lithium diisopropylamide. Other examples or suitable bases include potassium carbonate, potassium hydroxide, tertiary amines, guanidines, metal alkoxides and sodium hydride. Sodium methoxide and potassium t-butoxide are particularly suitable.

The temperature of the reaction to form III may be −80 to +100° C. with −15 to 25° C. being most suitable.

The solvent for the reaction to form compound III may be any liquid stable to the base. Examples are toluene, ether, acetonitrile, tetrahydrofuran (THF), and dimethylformamide (DMF).

For the reaction to form compound IV, the same solvents may be employed. Suitable reaction temperatures range from −20 to +200° C. with 0 to 50° C. desirable.

The reaction is accomplished by combining (III) with the arylhydrazine and treating with a dehydrating agent followed by an acid or base. Suitable acids or bases include acetic acid, hydrochloric acid, sulfuric acid, sodium methoxide, sodium ethoxide, 1,8-diazabicyclo[5.4.0]undec-7-ene (DBU), and tetramethylguanidine. Suitable dehydrating agents are described in *Reagents for Organic Synthesis*, John Wiley and Sons, New York, N.Y., (1968) p 1307, and include peptide coupling agents such as dicyclohexylcarbodiimide (DCC) and propanephosphonic acid anhydride. In one embodiment, DCC is added to (III) and arylhydrazine followed by the base, DBU.

Examples of compounds of formula (III) are as follows:

| Compound | Ar | Y | R | 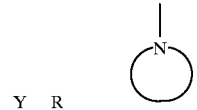 |
|---|---|---|---|---|
| III-1 | phenyl | O | —$C_2H_5$ | 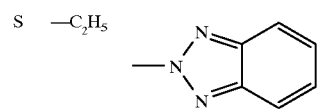 |
| III-2 | phenyl | S | —$C_2H_5$ | 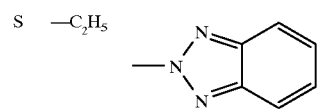 |
| III-3 | 4-nitrophenyl | O | —$CH_3$ | 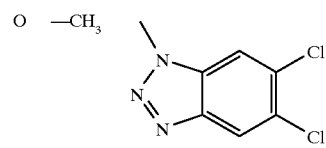 |
| III-4 | 4-nitrophenyl | S | —$C_2H_5$ | 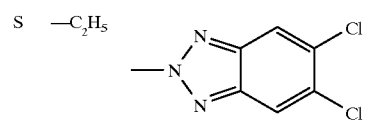 |

-continued

| Compound | Ar | Y | R | ![N-ring] |
|---|---|---|---|---|
| III-5 | 2,4-dichlorophenyl | O | —C$_2$H$_5$ | 1-methyl-5,6-dichlorobenzotriazole |
| III-6 | 2,4-dichlorophenyl | S | —C$_2$H$_5$ | 1-methyl-5,6-dichlorobenzotriazole |
| III-7 | 4-chloro-3-methyl-(NHCOC$_{13}$H$_{27}$-n)phenyl | S | —CH$_3$ | 1-methyl-5-(COOC$_6$H$_5$)benzotriazole |
| III-8 | 4-methyl-(NHCOC$_{13}$H$_{27}$-n)phenyl | S | —CH$_3$ | 1-methyl-5-(COOC$_6$H$_5$)benzotriazole |
| III-9 | 4-nitrophenyl | S | —C$_6$H$_5$ | pyrazolotriazole with C(=O)C$_6$H$_5$ and CH$_3$ |
| III-10 | 4-methyl-(NHCOC$_{13}$H$_{27}$-n)phenyl | O | —C$_6$H$_5$ | pyrazolotriazole with CH(OH)C$_6$H$_5$ and CH$_3$ |

-continued

| Compound | Ar | Y | R | ![heterocycle] |
|---|---|---|---|---|
| III-11 | 4-chloro-3-methyl / 2,4-di-sec-butyl phenyl with -NHCOC₂H₅ linker (see structure) | S | —C₂H₅ | 1-methyl-pyrrolo-triazole with C(=O)C₆H₅ and CH₃ substituents |
| III-12 | 4-nitrophenyl | S | —C₂H₅ | 1-methyl-1,2,4-triazol-3-yl-SCH₂C₆H₅ |
| III-13 | 4-methylphenyl-NHCOC₁₃H₂₇-n | S | —C₂H₅ | 1-methyl-1,2,4-triazol-3-yl-SCH₂C₆H₅ |
| III-14 | 4-methylphenyl-NHCOC₁₃H₂₇-n | S | —C₄H₉ | 1-methyl-1,2,4-triazol-3-yl-N=N-C₆H₄-N(CH₃)₂ |
| III-15 | 4-nitrophenyl | S | —CH₃ | 1-methyltetrazol-5-yl |
| III-16 | 4-nitrophenyl | S | —C₆H₆ | 1-methylimidazol-2-yl |

| Compound | Ar | Y | R | ⌬N (ring) |
|---|---|---|---|---|
| III-17 | 4-nitrophenyl | S | —C$_2$H$_5$ | pyrazolyl (N—N) |
| III-18 | 4-nitrophenyl | S | —C$_2$H$_5$ | triazolyl (N—N=N) |

Corresponding compounds of formula (IV) would include the foregoing compounds with Ar$^1$ groups such as phenyl or naphthyl groups.

Unless otherwise specifically stated, when a substituent group contains a substitutable hydrogen, it is intended to encompass not only the substituent's unsubstituted form, but also its form further substituted with any group or groups as herein mentioned. Suitably, a substituent group may be halogen or may be bonded to the remainder of the molecule by an atom of carbon, silicon, oxygen, nitrogen, phosphorous, or sulfur. The substituent may be, for example, halogen, such as chlorine, bromine or fluorine; nitro; hydroxyl; cyano; carboxyl; or groups which may be further substituted, such as alkyl, including straight or branched chain alkyl, such as methyl, trifluoromethyl, ethyl, t-butyl, 3-(2,4-di-t-pentylphenoxy) propyl, and tetradecyl; alkenyl, such as ethylene, 2-butene; alkoxy, such as methoxy, ethoxy, propoxy, butoxy, 2-methoxyethoxy, sec-butoxy, hexyloxy, 2-ethylhexyloxy, tetradecyloxy, 2-(2,4di-t-pentylphenoxy)ethoxy, and 2-dodecyloxyethoxy; aryl such as phenyl, 4-t-butylphenyl, 2,4,6-trimethylphenyl, naphthyl; aryloxy, such as phenoxy, 2-methylphenoxy, alpha- or beta-naphthyloxy, and 4-tolyloxy; carbonamido, such as acetamido, benzamido, butyramido, tetradecanamido, alpha-(2,4-di-t-pentylphenoxy)acetamido, alpha-(2,4-di-t-pentylphenoxy) butyramido, alpha-(3-pentadecylphenoxy)-hexanamido, alpha-(4-hydroxy-3-t-butylphenoxy)-tetradecanamido, 2-oxo-pyrrolidin-1-yl, 2-oxo-5-tetradecylpyrrolin-1-yl, N-methyltetradecanamido, N-succinimido, N-phthalimido, 2,5-dioxo-1-oxazolidinyl, 3-dodecyl-2,5-dioxo-1-imidazolyl, and N-acetyl-N-dodecylamino, ethoxycarbonylamino, phenoxycarbonylamino, benzyloxycarbonylamino, hexadecyloxycarbonylamino, 2,4-di-t-butylphenoxycarbonylamino, phenylcarbonylamino, 2,5-(di-t-pentylphenyl)carbonylamino, p-dodecylphenylcarbonylamino, p-toluylcarbonylamino, N-methylureido, N,N-dimethylureido, N-methyl-N-dodecylureido, N-hexadecylureido, N,N-dioctadecylureido, N,N-dioctyl-N'-ethylureido, N-phenylureido, N,N-diphenylureido, N-phenyl-N-p-toluylureido, N-(m-hexadecylphenyl)ureido, N,N-(2,5-di-t-pentylphenyl)-N'-ethylureido, and t-butylcarbonamido; sulfonamido, such as methylsulfonamido, benzenesulfonamido, p-toluylsulfonamido, p-dodecylbenzenesulfonamido, N-methyltetradecylsulfonamido, N,N-dipropylsulfamoylamino, and hexadecylsulfonamido; sulfamoyl, such as N-methylsulfamoyl, N-ethylsulfamoyl, N,N-dipropylsulfamoyl, N-hexadecylsulfamoyl, N,N-dimethylsulfamoyl; N-[3-(dodecyloxy)propyl]sulfamoyl, N-[4-(2,4-di-t-pentylphenoxy)butyl]sulfamoyl, N-methyl-N-tetradecylsulfamoyl, and N-dodecylsulfamoyl; carbamoyl, such as N-methylcarbamoyl, N,N-dibutylcarbamoyl, N-octadecylcarbamoyl, N-[4-(2,4-di-t-pentylphenoxy)butyl]carbamoyl, N-methyl-N-tetradecylcarbamoyl, and N,N-dioctylcarbamoyl; acyl, such as acetyl, (2,4-di-t-amylphenoxy)acetyl, phenoxycarbonyl, p-dodecyloxyphenoxycarbonyl methoxycarbonyl, butoxycarbonyl, tetradecyloxycarbonyl, ethoxycarbonyl, benzyloxycarbonyl, 3-pentadecyloxycarbonyl, and dodecyloxycarbonyl; sulfonyl, such as methoxysulfonyl, octyloxysulfonyl, tetradecyloxysulfonyl, 2-ethylhexyloxysulfonyl, phenoxysulfonyl, 2,4-di-t-pentylphenoxysulfonyl, methylsulfonyl, octylsulfonyl, 2-ethylhexylsulfonyl, dodecylsulfonyl, hexadecylsulfonyl, phenylsulfonyl, 4-nonylphenylsulfonyl, and p-toluylsulfonyl; sulfonyloxy, such as dodecylsulfonyloxy, and hexadecylsulfonyloxy; sulfinyl, such as methylsulfinyl, octylsulfinyl, 2-ethylhexylsulfinyl, dodecylsulfinyl, hexadecylsulfinyl, phenylsulfinyl, 4-nonylphenylsulfinyl, and p-toluylsulfinyl; thio, such as ethylthio, octylthio, benzylthio, tetradecylthio, 2-(2,4-di-t-pentylphenoxy) ethylthio, phenylthio, 2-butoxy-5-t-octylphenylthio, and p-tolylthio; acyloxy, such as acetyloxy, benzoyloxy, octadecanoyloxy, p-dodecylamidobenzoyloxy, N-phenylcarbamoyloxy, N-ethylcarbamoyloxy, and cyclohexylcarbonyloxy; amine, such as phenylanilino, 2-chloroanilino, diethylamine, dodecylamine; imino, such as 1-(N-phenylimido)ethyl, N-succinimido or 3-benzylhydantoinyl; phosphate, such as dimethylphosphate and ethylbutylphosphate; phosphite, such as diethyl and dihexylphosphite; a heterocyclic group, a heterocyclic oxy group or a heterocyclic thio group, each of which may be substituted and which contain a 3 to 7 membered heterocyclic ring composed of carbon atoms and at least one hetero atom selected from the group consisting of oxygen, nitrogen and sulfur, such as 2-furyl, 2-thienyl, 2-benzimidazolyloxy or 2-benzothiazolyl; quaternary ammonium, such as triethylammonium; and silyloxy, such as trimethylsilyloxy. If desired, the substituents may themselves be further substituted one or more times with the described substituent groups.
SYNTHESIS EXAMPLE
Synthesis Example 1
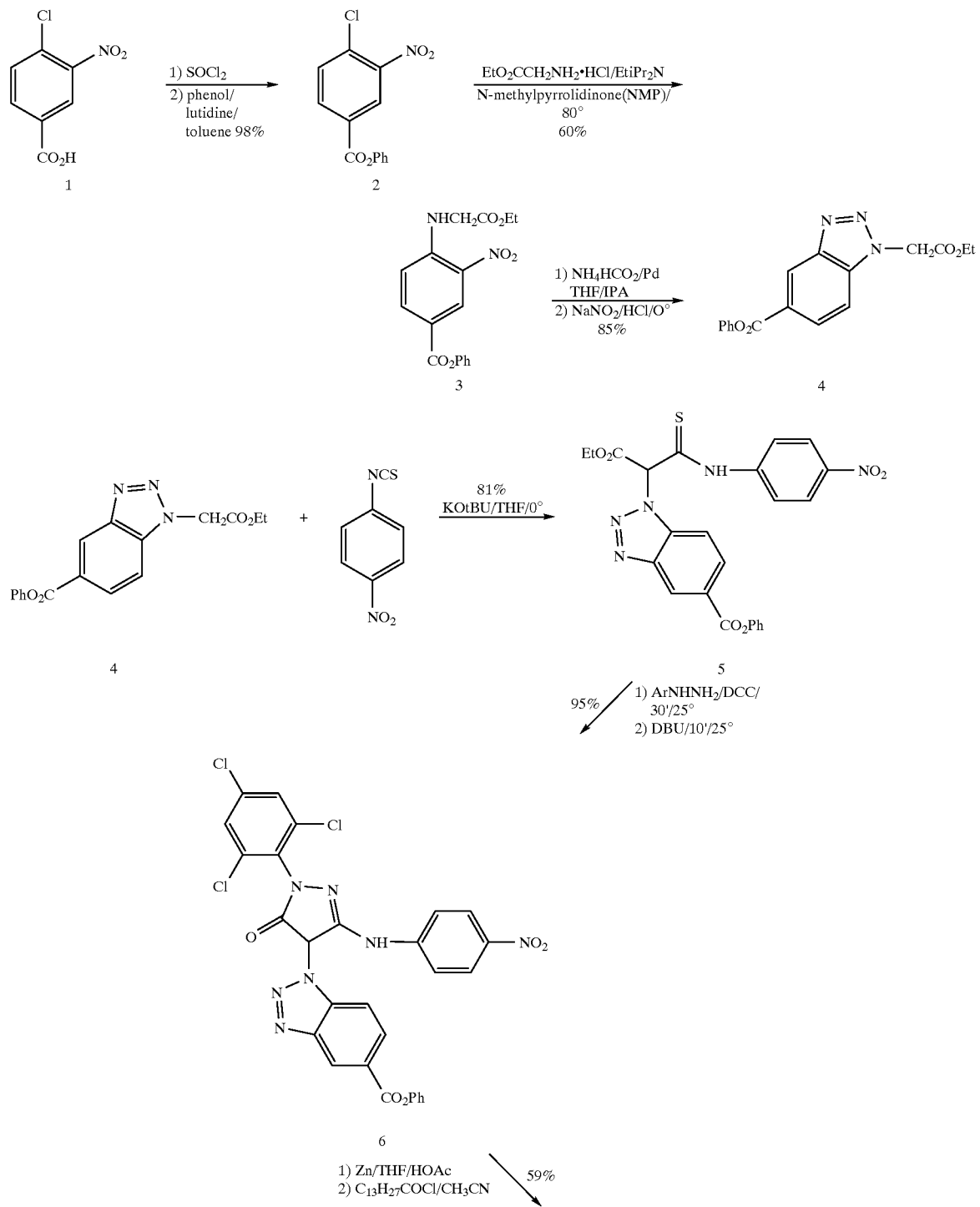

-continued

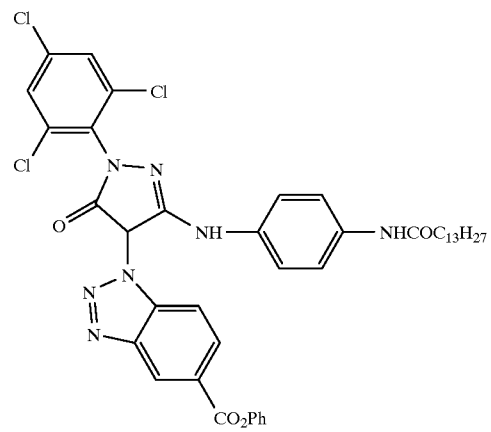

7

In the example, Et=ethyl, iPr=isopropyl, IPA=isopropyl alcohol, Ph=phenyl, tBu=t-butyl, Ar=aryl as indicated, Ac=acetyl and all temperatures are centigrade.

A mixture of 3-nitro-4-chlorobenzoic acid (1,72.4 g, 0.36 mole), thionyl chloride (72 ml, 1.0 mole), and dimethylformamide (DMF, 5 drops) were heated under reflux for about 1 hr until a homogeneous mixture resulted. The mixture was concentrated under reduced pressure using heptane as a chaser to remove residual thionyl chloride. Solid acid chloride (79.5 g, 99%) was obtained.

The acid chloride (79.5 g, 0.36 mole) was dissolved in 100 ml of toluene before adding phenol (34 g, 0.36 mole) and then lutidine (43 g, 0.4 mole). After stirring 30 min, the mixture was diluted with about 500 ml of ethyl acetate, washed consecutively with 2 N HCl, 0.5 N $Na_2CO_3$, and water before drying and concentrating. Solid 3-nitro-4-chlorophenylbenzoate (2, 102 g, 99%) was obtained.

A mixture of ethyl diisopropylamine (43 ml, 0.25 mole), glycine ethyl ester hydrochloride (21 g, 0.15 mole), N-methylpyrrolidinone (100 ml), and phenyl ester 2 (27.8 g, 0.1 mole) was heated at 80° for 40 min. before cooling to rt. Cold water (260 ml) containing 40 ml of 2 N HCl was added to precipitate a yellow solid. The solid was filtered, slurried in methanol, filtered, and air dried to 20.7 g (60%) of nitro ester 3.

Nitro ester 3 (3.44 g, 0.010 mole) was dissolved in 25 ml of tetrahydrofuran (THF) and warmed to 50° using a mechanical stirrer, 500 ml flask, and warm water bath. Isopropyl alcohol (15 ml), 5% Pd/C (0.8 g), and ammonium formate (3.15 g, 0.05 mole) were added before stirring the mixture vigorously for 15 min at 50° until the yellow color of the nitro compound faded. The mixture was cooled immediately with an ice bath. A solution of sodium nitrite (0.83 g, 0.012 mole in 8 ml of water), 40 g of ice, and 8 ml of conc. HCl were added consecutively with vigorous stirring. After 5 min, the mixture was diluted with about 100 ml of cold water and filtered. The moist filter cake was dissolved in a minimum volume of THF, filtered to remove catalyst, diluted with water again to reprecipitate the product, filtered, and air dried to 2.85 g (88%) of benzotriazolyl diester 4. The reaction course can be followed by TLC using silica gel adsorbent with ethyl acetate: heptane (1:1) as eluent. The intermediate amino compound has a lower $r_f$ than the starting nitro diester but is transformed readily into the cyclic amide on silica gel. The amino compound is relatively stable in neutral or slightly alkaline media but ring closes readily in acidic solution. Cold, strongly acidic nitrous acid solutions, however, convert the amine rapidly to the benzotriazole via the diazonium salt. This reaction was repeated on larger scale (0.03 mole) with similar results (85% yield). The reduction step required 0.20 mole of ammonium formate with heating at 50° for 30 min.

A solution of diester 4 (6.5 g, 0.02 mole) and p-nitrophenylisothiocyanate (4.3 g, 0.024 mole) in THF (60 ml) in a three-neck flask fitted with thermometer, nitrogen inlet, and magnetic stir bar was cooled to −50° with a dry ice/isopropanol bath. Potassium t-butoxide (2.6 g, 0.023 mole) was added to the mixture before allowing it to warm slowly to about 10°. [The deep red color initially present faded to a yellow-orange color as the reaction progressed. The course of the reaction could also be followed by TLC (silica gel) using 2:1 heptane:ethyl acetate (plus a little acetic acid to reduce streaking) as eluent. The thioamide product is yellow, is less mobile than either starting material, and couples slowly with Dox to give an orange dye.] Ice (50 g), 1 N $NaHCO_3$ (30 ml), water (100 ml), and heptane (150 ml) were then added to the mixture before stirring vigorously. The orange aqueous layer was separated and treated with 30 ml of 12 N HCl to precipitate the product as a gum which could be induced to crystallize by the addition of diethyl ether. A total of 8.2 g (81%) of adduct 5 was obtained. Subsequent experiments showed that this reaction proceeded equally well using DMF as solvent with molecular sieves present to absorb water at a preparatively more practical reaction temperature of 0°. Bases such as sodium methoxide or potassium carbonate also worked but the reaction was generally slower.

Trichlorophenylhydrazine (4.65 g, 0.022 mole) and adduct 5 (10.67 g, 0.021 mole) were combined in 100 ml of THF and cooled to 10° before adding dicyclohexylcarbodiimide (4.5 g, 0.022 mole), warming to room temperature, and stirring for 30 min. The hydrazone intermediate was converted to pyrazolone by addition of 1,8-diazabicylo[5.4.0]undec-7-ene (DBU, 3.2 g, 0.021 mole) to the mixture and stirring for 10 min. Product was precipitated as a gum by the addition of cold aqueous HCl. The gum solidified when slurried with acetonitrile to yield a powder which was contaminated with dicyclohexylthiourea. This powder was boiled with 500 ml of diethyl ether and 10 ml of triethylamine for about 15 min and then filtered to remove most of the thiourea. The crude solid filter cake was boiled with 100 ml of methanol and 10 ml of acetic acid, cooled, and filtered to yield the desired coupler 6 as a yellow powder (12.7 g, 95%).

Reduction of the nitro group proceeded by heating a mixture of coupler 6 (7.5 g, 0.012 mole), zinc dust (8 g, 0.12 mole), 100 ml of THF, and 20 ml of acetic acid to reflux for a few minutes until the yellow color of the nitro coupler faded. The mixture was cooled, diluted with water, and shaken with ethyl acetate. The organic layer was decanted from the water and solid zinc residue. After washing with aqueous bicarbonate and water, the extract was dried over $MgSO_4$ and concentrated to a solid. The solid was crystallized from methanol to yield 6.1 g (85%) of coupler amine.

Coupler amine (6.9 g, 0.0113 mole) was dissolved in a mixture of THF (20 ml), acetonitrile (40 ml), and toluene (20 ml) and treated with myristoyl chloride (3.0 g, 0.012 mole). The mixture was heated to reflux for about 5 min to complete the reaction and then concentrated to a syrup. Addition of methanol caused crystallization of the product 7 (5.7 g, 59%).

The entire contents of the patent applications, patents and other publications referred to in this specification are incorporated herein by reference.

What is claimed is:

1. A compound having formula (III)

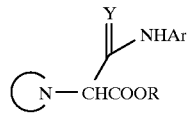

(III)

wherein:

R is an alkyl or aryl group;

C represents the nonmetallic atoms necessary to complete an azole ring;

Ar represents an aromatic carbocyclic or an aromatic heterocyclic group; and

Y represents an atom of sulfur.

2. The compound of claim 1 wherein R is an alkyl group.

3. The compound of claim 1 wherein Ar is a phenyl group.

4. The compound of claim 1 wherein the Ar group has a substituent selected from the group consisting of nitro, chloro, fluoro, alkyl, carbonamido, cyano, ester, sulfonyl, and sulfonamido groups.

5. The compound of claim 1 wherein C represents the nonmetallic atoms necessary to form a triazole, an imidazole, a tetrazole, or a pyrazole group.

6. The compound of claim 5 wherein C represents the nonmetallic atoms necessary to form a 1,2,4-triazole, or a 1,2,3-triazole group.

7. The compound of claim 5 wherein the triazole is a benzotriazole group.

8. The compound of claim 7 wherein said benzotriazole group is substituted.

* * * * *